(12) United States Patent
Hsieh et al.

(10) Patent No.: US 8,940,333 B2
(45) Date of Patent: *Jan. 27, 2015

(54) AMPHIPHILIC BLOCK COPOLYMERS AND NANOPARTICLES COMPRISING THE SAME

(75) Inventors: Ming-Fa Hsieh, Hsinchu (TW); Hsuen-Tseng Cha'ng, Kaohsiung (TW); Chin-Fu Chen, Taipei County (TW); Yuan-Chia Chang, Taipei (TW); Pei Kan, Hsinchu (TW); Tsai-Yu Lin, Changhua County (TW)

(73) Assignee: Industrial Technology Research Institute, Hsinchu (TW)

( * ) Notice: Subject to any disclaimer, the term of this patent is extended or adjusted under 35 U.S.C. 154(b) by 1469 days.

This patent is subject to a terminal disclaimer.

(21) Appl. No.: 12/053,327

(22) Filed: Mar. 21, 2008

(65) Prior Publication Data

US 2008/0166382 A1 Jul. 10, 2008

Related U.S. Application Data

(63) Continuation-in-part of application No. 11/268,544, filed on Nov. 8, 2005.

(51) Int. Cl.
*A61K 9/14* (2006.01)
*A61K 9/51* (2006.01)
(Continued)

(52) U.S. Cl.
CPC ............. *A61K 9/5153* (2013.01); *A61K 9/1075* (2013.01); *A61K 47/34* (2013.01); *C08G 63/664* (2013.01); *C08G 63/6852* (2013.01); *C08G 63/6882* (2013.01); *C08G 63/6922* (2013.01); *Y10S 977/906* (2013.01); *Y10S 977/926* (2013.01)
USPC ............. 424/489; 424/46; 514/283; 525/437; 525/54.2; 977/906; 977/926

(58) Field of Classification Search
None
See application file for complete search history.

(56) References Cited

U.S. PATENT DOCUMENTS 5,543,158 A 8/1996 Gref et al.
5,741,852 A 4/1998 Marchant et al.
(Continued)

FOREIGN PATENT DOCUMENTS

WO WO 03/074026 A1 9/2003

OTHER PUBLICATIONS

Mori et la. Use of phosphobetaine type zwitterionic surfactant for the use of alkali and alkali earth metal ions and ammonium ions in human saliva by capillary electrophoresis. Anal Bioanal chem. 2003, 374:75-79.*

(Continued)

*Primary Examiner* — Lakshmi Channavajjala
(74) *Attorney, Agent, or Firm* — Muncy, Geissler, Olds & Lowe, P.C.

(57) ABSTRACT

An amphiphilic block copolymer is disclosed. The amphiphilic block copolymer includes one or more hydrophilic polymers, one or more hydrophobic polymer, and one or more zwitterions. The invention also provides a nanoparticle and carrier including the amphiphilic block copolymer for delivery of water insoluble drugs, growth factors, genes, or water insoluble cosmetic substances.

5 Claims, 6 Drawing Sheets

(51) Int. Cl.
*A61K 31/00* (2006.01)
*C08G 63/91* (2006.01)
*C08G 63/48* (2006.01)
*A61K 8/11* (2006.01)
*A61K 9/107* (2006.01)
*A61K 47/34* (2006.01)
*C08G 63/664* (2006.01)
*C08G 63/685* (2006.01)
*C08G 63/688* (2006.01)
*C08G 63/692* (2006.01)
*A61K 8/00* (2006.01)
*A61K 9/12* (2006.01)

(56) References Cited

U.S. PATENT DOCUMENTS 6,007,845 A 12/1999 Domb et al.
6,204,324 B1 3/2001 Shuto et al.
6,322,805 B1* 11/2001 Kim et al. .................... 424/426
8,124,128 B2* 2/2012 Hsieh et al. .................. 424/489

OTHER PUBLICATIONS

Nederberg et al. "Synthesis, Characterization, and Properties of Phosphoryl Choline Functionalized Poly∈-Caprolactone and Charged Phospholipid Analogues"; Macromolecules; 37:954-965 (2004).*

* cited by examiner

AMPHIPHILIC BLOCK COPOLYMERS AND NANOPARTICLES COMPRISING THE SAME

This application is a Continuation-In-Part of pending U.S. patent application Ser. No. 11/268,544, filed Nov. 8, 2005, and entitled "Amphiphilic block copolymers and nanoparticles comprising the same".

BACKGROUND OF THE INVENTION

1. Field of the Invention

The invention relates to a polymer, and more specifically to a biocompatible and biodegradable block copolymer and a nanoparticle comprising the same.

2. Description of the Related Art

To improve curative effects and reduce side effects, an optimal drug delivery carrier capable of precisely targeting tumor cells and producing high drug concentration around the focus is required. Such carrier materials must be biocompatible, biodegradable, and undetectable by the immune system to avoid macrophage attack. Common carrier materials comprise block copolymers. Some, however, lack biodegradability, long term stability, and are detectable to immune cells circulating in the blood.

Sugiyama provides a zwitterionic copolymer comprising a hydrophilic chain of 2-(methacryloyloxy)ethyl phosphorylcholine (MPC) and a hydrophobic chain ends of cholesteryl with critical micelle concentration (CMC) of $2.5 \times 10^{-4}$-$2.7 \times 10^{-5}$ wt % recited in Journal of Polymer Science Part A: Polymer Chemistry (2003) 1992-2000. Such material forms a complex with cholesterol molecules in condensed layer morphology with a 3.52 nm interval therebetween. This copolymer provides hemocompatibility and encapsulates water insoluble drugs by hydrophobic cholesterol groups attached on the polymer chains. The material, however, lacks biodegradability.

Stenzel provides a zwitterionic block copolymer comprising poly(2-acryloyloxyethyl phosphorylcholine) and poly (butyl acrylate) with biocompatibility formed by reversible addition fragmentation transfer (RAFT) recited in Macromolecular Bioscience (2004) 445-453. The nanoparticle formed in water and methanol binary solvent thereby has a diameter of about 40-160 nm. This copolymer, however, also lacks biodegradability.

Nakabayashi provides a biodegradable poly(L-lactic acid) (PLLA) material comprising phosphorylcholine such as L-α-glycerophosphorylcholine (LGPC) recited in Journal of Biomedical Materials Research part A (2003) 164-169. Various molecular weight PLLA materials can be polymerized using LGPC as an initiator. According to a blood cell experiment, as the phosphorylcholine content of PLLA increases, blood-cell adsorption decreases. Thais material, however, lacks micelle characteristics.

Oishi provides a novel zwitterionic poly(fumaramate) material comprising phosphorylcholine with CMC of about $1.7 \times 10^{-3}$-$1.0 \times 10^{-3}$ M recited in Polymer (1997) 3109-3115. Conducting isopropyl and methyl groups to fumaramate alters the CMC. According to a bovine serum albumin adsorption experiment, as the phosphorylcholine content of poly(fumaramate) increases, bovine serum albumin adsorption is reduced.

Sommerdijk provides a polystyrene material comprising tetra(ethylene glycol) and phosphorylcholine bonded to its side chain with biocompatibility recited in Journal of Polymer Science Part A: Polymer Chemistry (2001) 468-474. According to a protein adsorption experiment and in vitro human dermal fibroblast culture, only polystyrene material containing tetra(ethylene glycol) and phosphorylcholine can reduce protein adsorption and fibroblast growth, as compared with polystyrene bonded with tetra(ethylene glycol) or phosphorylcholine alone.

Langer provides a biodegradable injection-type nanoparticle comprising diblock (AB) or triblock (ABC) copolymer disclosed in U.S. Pat. Nos. 5,543,158 and 6,007,845. A is a hydrophilic chain such as poly(alkylene glycol), B is a hydrophobic chain such as PLGA, and C is a bioactive substance such as antibody. The particle can target cells or organs by the bioactive substance bonded thereto. These applications, however, fail to disclose that AB or ABC provide invisibility to biorecognition.

Kim provides a biodegradable drug-contained micelle comprising diblock (BA) or triblock (ABA or BAB) copolymer with a preferable molecular weight of about 1430-6000 and a hydrophilic chain ratio of 50-70 wt % disclosed in U.S. Pat. No. 6,322,805. A is a biodegradable hydrophobic chain and B is a hydrophilic chain such as PEG. Drugs such as paclitaxel are physically encapsulated. The application, however, fails to disclose an ABC-type triblock copolymer.

Marchant provides an anti-thrombosis triblock copolymer comprising a hydrophobic biodegradable polymer and a hydrophilic polysaccharide chain such as dextran or heparin disclosed in U.S. Pat. No. 5,741,852.

Ishihara provides a method for preparing a phosphorylcholine-contained polymer in aqueous phase disclosed in U.S. Pat. No. 6,204,324. Adding initiator in aqueous medium polymerizes polymerizable monomers, phosphorylcholine. A separation film, containing impurity of less than 2000 ppm, then purifies the results.

BRIEF SUMMARY OF THE INVENTION

The invention provides a block copolymer comprising one or more hydrophobic blocks and one or more zwitterions.

The invention provides a block copolymer comprising one or more hydrophilic blocks, one or more hydrophobic blocks, and one or more zwitterions, wherein the hydrophilic block is bonded to the hydrophobic block.

The invention also provides a nanoparticle comprising one or more of the disclosed block copolymers.

The invention further provides a nanocarrier comprising the disclosed nanoparticle and an active substance encapsulated in the particle.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawing, wherein.

DETAILED DESCRIPTION OF THE INVENTION

Figure 1:
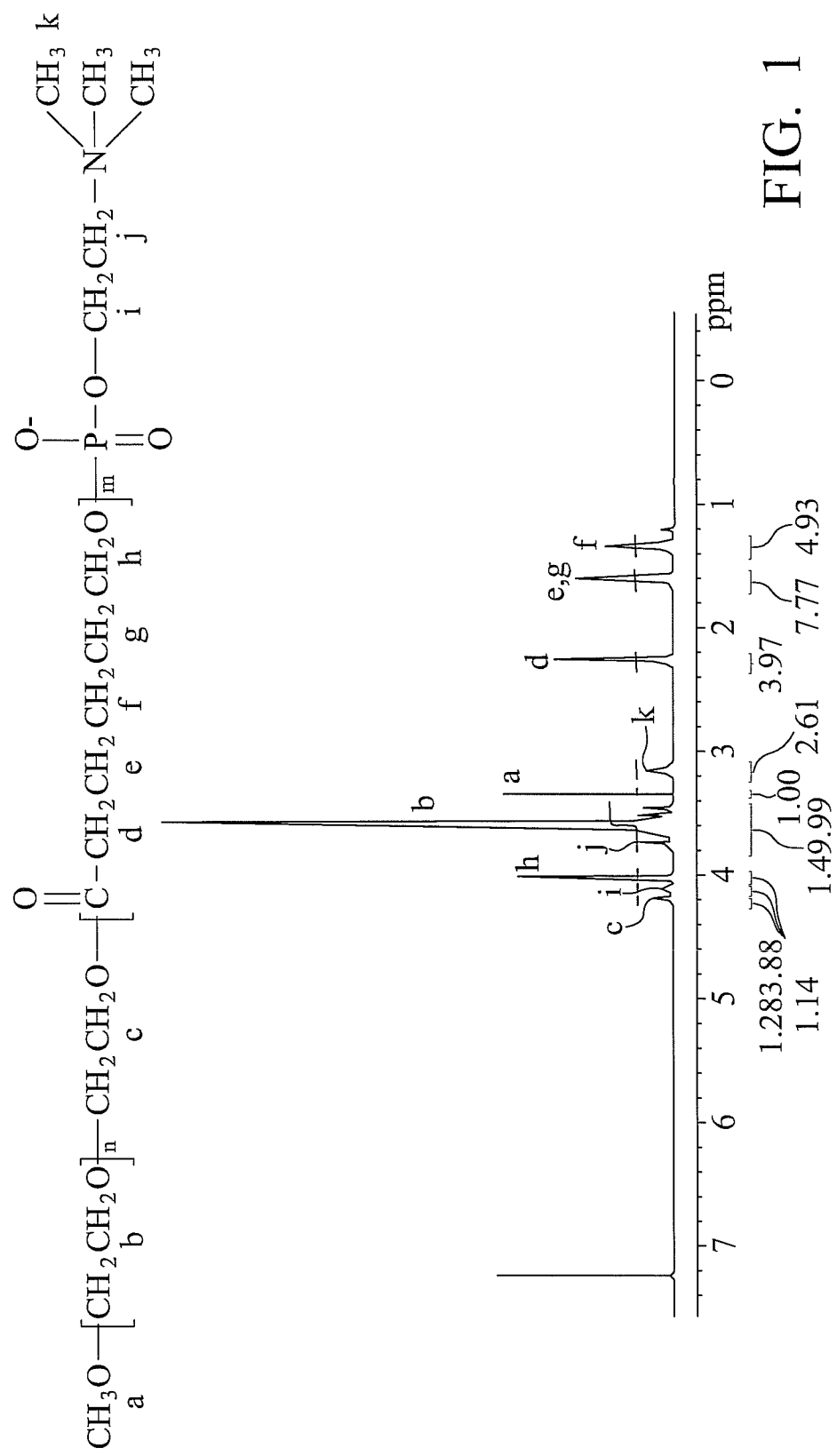
FIG. 1 shows $^1$H-NMR spectrum of PEG-PCL-PC.

The following description is of the best-contemplated mode of carrying out the invention. This description is made for the purpose of illustrating the general principles of the invention and should not be taken in a limiting sense. The scope of the invention is best determined by reference to the appended claims.

One embodiment of the invention provides a block copolymer comprising one or more hydrophobic polymers and one or more zwitterions.

The copolymer is an amphiphilic block copolymer. The block copolymer comprises diblock copolymer, with CMC of about 0.1-0.01 wt %. The hydrophobic block has a molecular weight of about 1,000-30,000 and may comprise polyester such as polycaprolactone (PCL), polyvalerolactone (PVL), poly(lactide-co-glycolide) (PLGA), polylactic acid (PLA), polybutyrolactone (PBL), polyglycolide, and polypropiolactone (PPL). The zwitterions may comprise phosphorylcholine (PC), sulfobetaine (NS), or amino acids.

The block copolymer further comprises one or more hydrophilic blocks bonded to the hydrophobic block to form a triblock copolymer of hydrophilic block-hydrophobic block-zwitterion. The hydrophilic block has a molecular weight of about 550-20,000 and may comprise polyethylene glycol (PEG), hyaluronic acid (HA), or poly-γ-glutamic acid (γ-PGA). The block copolymer comprising diblock or triblock is biodegradable and biocompatible.

One embodiment of the invention provides a block copolymer comprising one or more hydrophilic blocks, one or more hydrophobic blocks, and one or more zwitterions. In this copolymer structure, the hydrophilic block is bonded to the hydrophobic block.

One embodiment of the invention provides a nanoparticle comprising one or more of the disclosed block copolymers.

The nanoparticle has a hydrophobic interior and hydrophilic surface and its diameter is about 20-1,000 nm.

Due to the chain flexibility of hydrophilic blocks in blood, zwitterions capable of maintaining particle structure without being recognized by immune cells during a drug release period, and a hydrophobic block decomposable by enzymes or hydrolysis of the novel biomedical nanoparticle provides biocompatibility, biodegradability, and invisibility to immune cells. After the hydrophobic block is decomposed, remaining harmless substances such as hydrophilic block and zwitterion are dissolved in blood and then removed from the renal system.

One embodiment of the invention provides a nanocarrier comprising the disclosed nanoparticle and an active substance encapsulated in the particle.

The active substance may comprise water insoluble drugs such as camptothecin or derivatives thereof, growth factors, genes, or water insoluble cosmetic substances such as ingredients for skill care. The nanocarrier can be delivered by oral, transdermal administration, injection, or inhalation.

The preparation of the biomedical polymer is described as follows. First, a copolymer comprising a hydrophilic block and a hydrophobic block, such as PEG-PCL, PEG-PVL, and PEG-PPL, is prepared. Next, the copolymer is dissolved in a solvent, such as dichloromethane ($CH_2Cl_2$), and its terminal is added with a chemical group, such as 2-chloro-2-oxo-1,3,2-dioxaphospholane (COP), succinic anhydride (SA), and 3-(dimethylamino)propylamine (DMAPA), to form a modified copolymer. After the modified copolymer is dissolved in a solvent such as acetonitrile and chloroform, its modified terminal is reacted with another chemical group, such as trimethylamine (TMA), 1,3-propane sultone (PS), and benzyl histidine, to form zwitterions. Thus, a copolymer comprising a hydrophilic block, a hydrophobic block, and zwitterions is obtained.

EXAMPLES

Example 1

Synthesis of PEG-PCL-PC

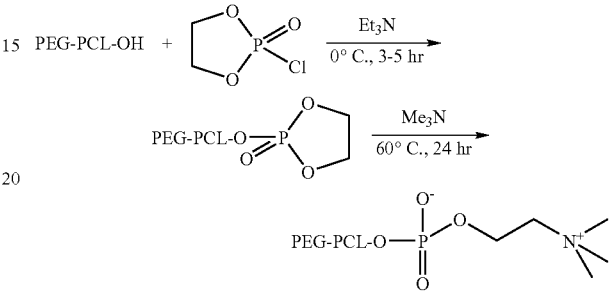

(1) Polymerization of PEG-PCL:

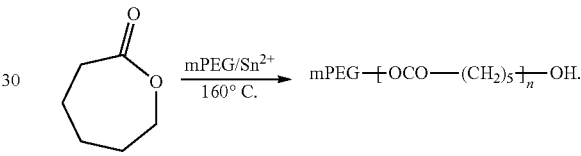

60 g poly(ethylene glycol) (PEG, 5000 g/mole) and 12 g ε-caprolactone were added to a 250 ml glass reactor (8 cm×8 cm×10 cm) with gradual heating until totally dissolved. The PEG-PCL polymerization then began by adding 0.38 mL catalyst of stannous 2-ethylhexanoate at 160° C. for 24 hours. Dissolving in dichloromethane and re-precipitating in diethyl ether purified the crude product. The purification was repeated three times and vacuum-dried at 40° C. for 24 hours. Thus, a PEG-PCL copolymer was obtained.

(2) Synthesis of PEG-PCL-COP:

5 g PEG-PCL copolymer and 0.43 g triethylamine (TEA) were dissolved in 70 ml dichloromethane at 0° C. with mechanical stirring in a 250 ml flask. Another solution containing 3.5 g 2-chloro-2-oxo-1,3,2-dioxaphospholane (COP) dissolved in 30 ml dichloromethane was prepared simultaneously. The COP-containing solution was then gradually dropped into the flask within 1 hour and reacted at 0° C. for 4 hours. The resulting solution was then warmed to room temperature and filtered by 0.45 μm filter paper to remove the by-product, triethylammonium chloride. After removing dichloromethane, a modified copolymer, PEG-PCL-COP, was obtained.

(3) Synthesis of PEG-PCL-PC:

PEG-PCL-COP was dissolved in 70 ml acetonitrile at room temperature in a flask. 10 ml trimethylamine (33% in ethanol) was then dropped into the flask and reacted at 60° C. for 24 hours with stirring. After removing the solvent, the resulting solution was extracted three times by dichloromethane/water. After removing dichloromethane and vacuum-drying for 24 hours, white solid resulted, PEG-PCL-PC copolymer, were obtained. Its $^1$H-NMR is shown in FIG. 1.

Example 2

Synthesis of PEG-PVL-PC

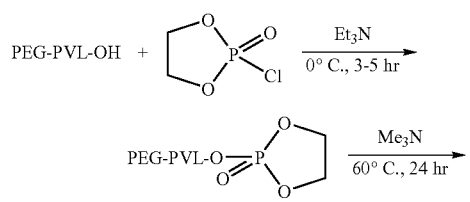

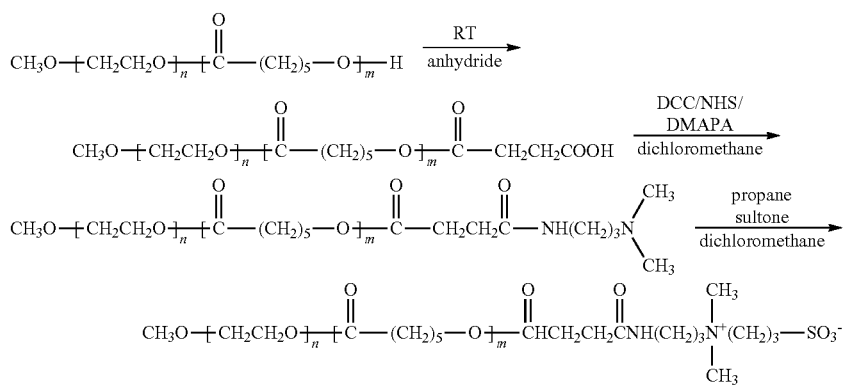

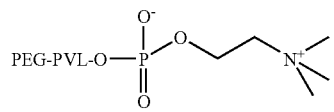

(1) Polymerization of PEG-PVL:

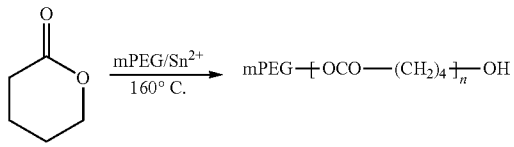

60 g poly(ethylene glycol) (PEG, 5000 g/mole) and 12 g δ-valerolactone were added to a 250 ml glass reactor (8 cm×8 cm×10 cm) with gradual heating until totally dissolved. The PEG-PVL polymerization then began by adding 0.38 ml catalyst of stannous 2-ethylhexanoate at 160° C. for 8 hours. The result was dissolved in dicholomethane and re-precipitated by adding diethyl ether. The white precipitate was then washed three times and vacuum-dried at 40° C. for 24 hours. Thus, a PEG-PVL copolymer was obtained.

(2) Synthesis of PEG-PVL-COP:

5 g PEG-PVL copolymer and 0.43 g triethylamine (TEA) were dissolved in 70 ml dichloromethane at 0° C. by mechanical stirring in a 250 ml flask. Another solution containing 3.5 g 2-chloro-2-oxo-1,3,2-dioxapholane (COP) dissolved in 30 ml dichloromethane was prepared simultaneously. The COP-containing solution was then gradually added to the flask over 1 hour and reacted at 0° C. for 6 hours. The resulting solution was then warmed to room temperature and filtered by 0.45 μm filter paper to remove the by-product, triethylammonium chloride. After removing dichloromethane, a modified copolymer, PEG-PVL-COP, was obtained.

(3) Synthesis of PEG-PVL-PC:

PEG-PVL-COP was dissolved in 70 ml acetonitrile at room temperature in a flask. 10 ml trimethylamine (33% in ethanol) was then dropped into the flask and reacted at 60° C. for 24 hours with stirring. After removing the solvent, the resulting solution was extracted three times by dichloromethane/water. After removing dichloromethane and vacuum-drying for 24 hours, white solid results, PEG-PVL-PC copolymer, were obtained.

Example 3

Synthesis of PEG-PCL-NS (1) Synthesis of PEG-PCL-SA:

3 g PEG-PCL copolymer and 0.1 g 4-dimethylaminopyridine (DMAP) were dissolved in 60 ml dichloromethane at 0° C. with mechanical stirring in a 250 ml flask. Another solution containing 0.1 g triethylamine (TEA) and 0.5 g succinic anhydride (SA) dissolved in 10 ml dichloromethane was prepared simultaneously. The SA-contained solution was then gradually dropped into the flask within 1 hour and reacted at 25° C. for 24 hours. The resulting solution was then precipitated three times by adding diethyl ether and vacuum-dried for 24 hours. Thus, a modified copolymer, PEG-PCL-SA, was obtained.

(2) Synthesis of PEG-PCL-TA:

2 g PEG-PCL-SA copolymer, 0.2 g 1,3-dicyclohexylcarbodiimide (DCC), and 0.1 g N-hydroxysuccinimide (NHS) were dissolved in 40 ml dichloromethane at 0° C. with mechanical stirring in a 250 ml flask. Another solution containing 0.1 g 3-(dimethylamino)propylamine (DMAPA) dissolved in 10 ml dichloromethane was prepared simultaneously. The DMAPA-contained solution was then gradually dropped into the flask within 1 hour and reacted at 25° C. for 24 hours. The resulting solution was then precipitated three times by adding diethyl ether and vacuum-dried for 24 hours. Thus, a modified copolymer, PEG-PCL-TA, was obtained.

Figure 2:
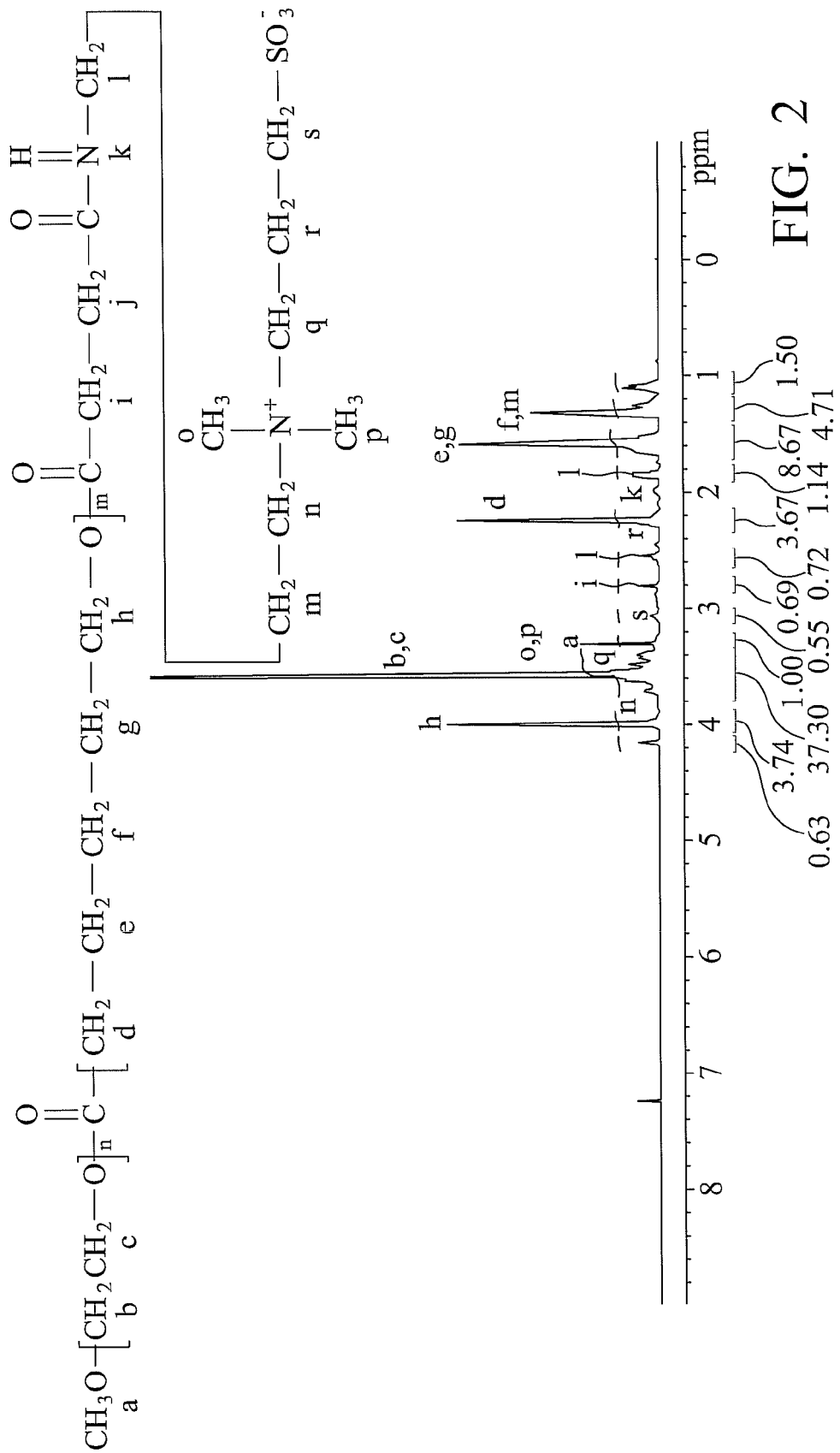
FIG. 2 shows $^1$H-NMR spectrum of PEG-PCL-NS.

(3) Synthesis of PEG-PCL-NS:

0.15 g PEG-PCL-TA was dissolved in 60 ml chloroform at 0° C. in a flask. 0.36 g 1,3-propane sultone (20% in chloroform) was then dropped into the flask and reacted at 30° C. for 24 hours with stirring. The resulting solution was then precipitated three times by adding diethyl ether and vacuum-dried for 24 hours. Thus, a copolymer, PEG-PCL-NS, was obtained. Its $^1$H-NMR is shown in FIG. 2.

Example 4

Synthesis of PEG-PCL-Benzyl Histidine

Coupling of PEG-PCL-SA and Benzyl Histidine

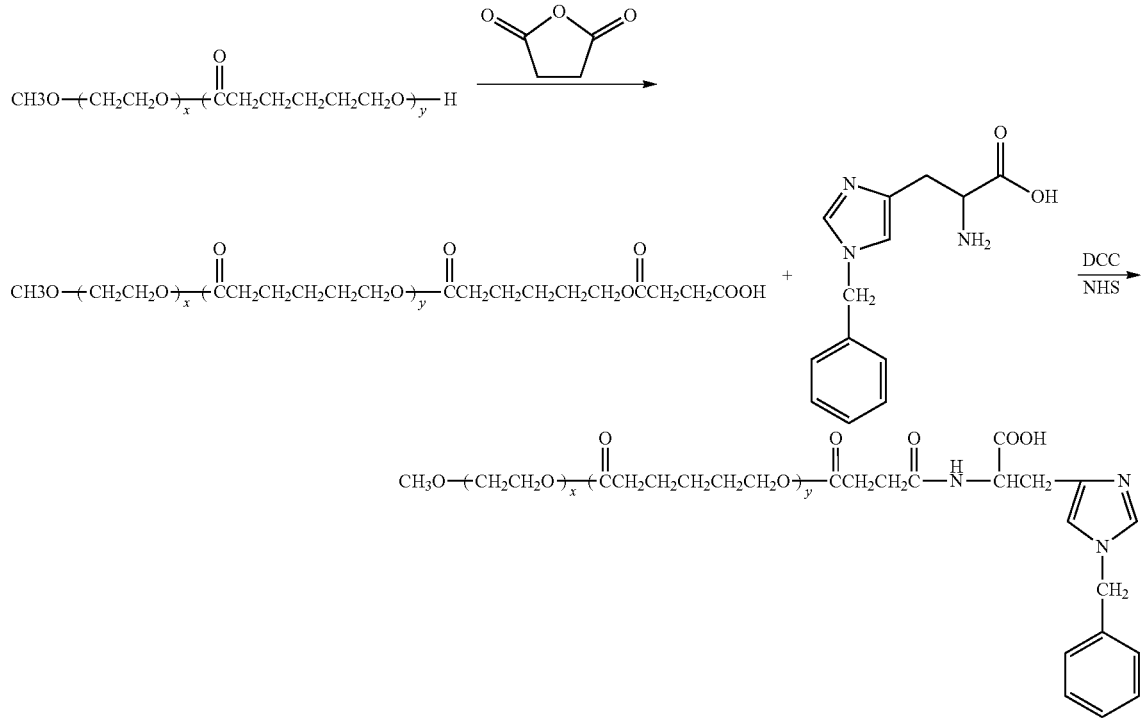

Figure 3:
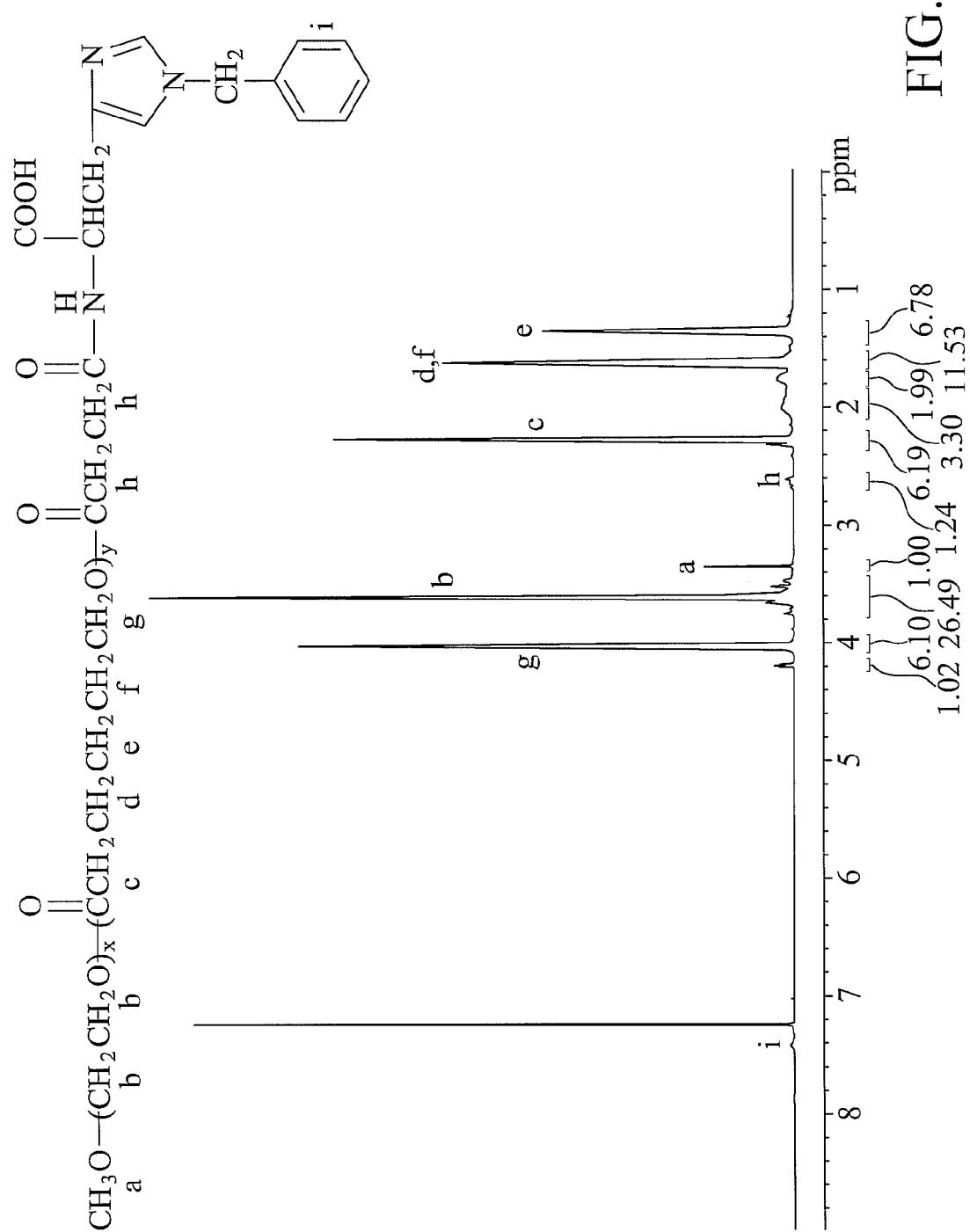
FIG. 3 shows $^1$H-NMR spectrum of PEG-PCL-benzyl histidine.

2 g PEG-PCL-SA copolymer, 0.1547 g N,N-dicyclohexyl carbodiimide (DCC) and 0.0863 g N-hydroxysuccinimide (NHS) were dissolved in 50 ml dichloromethane at 40° C. with mechanical stirring in a 250 ml flask. Another solution containing 0.368 g imbenzyl-L-histidine (His(Bzl)) dissolved in 100 ml methanol was prepared simultaneously. The His(Bzl)-contained solution was then added into the flask and reacted at 60° C. for 24 hours. The resulting solution was then cooled down to room temperature and filtered by 0.45 μm filter paper to remove the un-reaction material, His(Bzl). After removing dichloromethane, a modified copolymer, PEG-PCL-His(Bzl), was obtained. Its $^1$H-NMR is shown in FIG. 3.

Example 5

The Critical Micelle Concentration (CMC) Test of Polymeric Micelles

The micelle CMC was measured by the method recited in Jeong et al., 1999. 0.4 mM DPH (1,6-diphenyl-1,3,5-hexatriene) water solution and copolymers with $2-2\times10^{-4}$ wt % were mixed. Absorption in 356 nm of the water solution was then measured by a UV-Vis spectrometer. Finally, the absorption was plotted in a diagram against logarithm of polymer concentrations. A turning point formed by two various slopes in the diagram is CMC.

Table 1 recited CMC values of the block copolymers are shown here.

TABLE 1

| Sample ID | Molecular weight of PEG (g/mole) | Molecular weight of PCL (g/mole) | CMC ($\times 10^{-2}$ wt %) |
|---|---|---|---|
| PEG-PCL-PC1 | 5,000 | 1,900 | 3.26 |
| PEG-PCL-PC2 | 5,000 | 1,100 | 17.92 |
| PEG-PCL-PC3 | 750 | 2,100 | 3.43 |
| PEG-PCL-PC4 | 2,000 | 900 | 17.8 |
| PEG-PCL-PC5 | 5,000 | 13,000 | 1.7 |
| PEG-PCL-NS1 | 2,000 | 1,000 | 1.46 |
| PEG-PCL-NS2 | 2,000 | 2,000 | 4.47 |
| PEG-PCL-NS3 | 5,000 | 2,500 | 3.95 |
| PEG-PCL-NS4 | 5,000 | 3,700 | 7.76 |
| PEG-PCL-His(Bzl)1 | 5,000 | 2,500 | 5.46 |

Example 6

Preparation of Micelles and Analysis of Sizes Thereof 10 mg polymer was dissolved in 1 ml THF to form a solution. The solution was gradually dropped into 30 ml deionized water by a 2.5 ml syringe and stirred. The solution was then placed in a dialysis membrane to dialyze for 24 hours to form a micelle Solution. Finally, 3-5 ml of micelle solution was placed in an acrylic cuvette to measure micelle sizes and their distribution by a photon correlation spectroscopy (Malvern Instrument Zetasizer Nano ZS), as shown in Table 2.

TABLE 2

| Sample ID | Molecular weight of PEG (g/mole) | Molecular weight of PCL (g/mole) | Hydrodynamic diameter (nm) |
|---|---|---|---|
| PEG-PCL-PC1 | 5,000 | 1,900 | 113.8 |
| PEG-PCL-PC2 | 5,000 | 1,100 | — |
| PEG-PCL-PC3 | 750 | 2,100 | — |
| PEG-PCL-PC4 | 2,000 | 900 | 186 |
| PEG-PCL-PC5 | 5,000 | 13,000 | 164 |
| PEG-PCL-NS1 | 2,000 | 1,000 | 148.3 |
| PEG-PCL-NS2 | 2,000 | 2,000 | 34.7 |
| PEG-PCL-NS3 | 5,000 | 2,500 | 27.2 |
| PEG-PCL-NS4 | 5,000 | 3,700 | — |

Example 7

In Vitro Stealth Test

Figure 5:
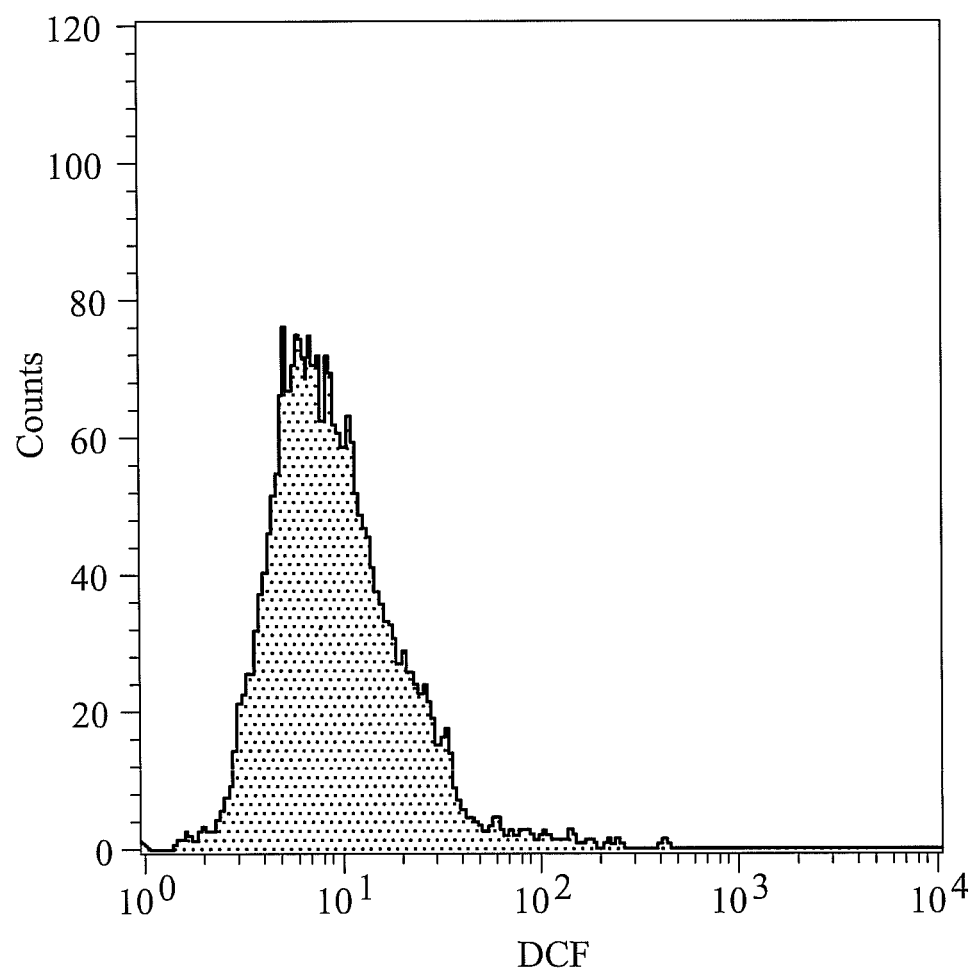
Figure 6:
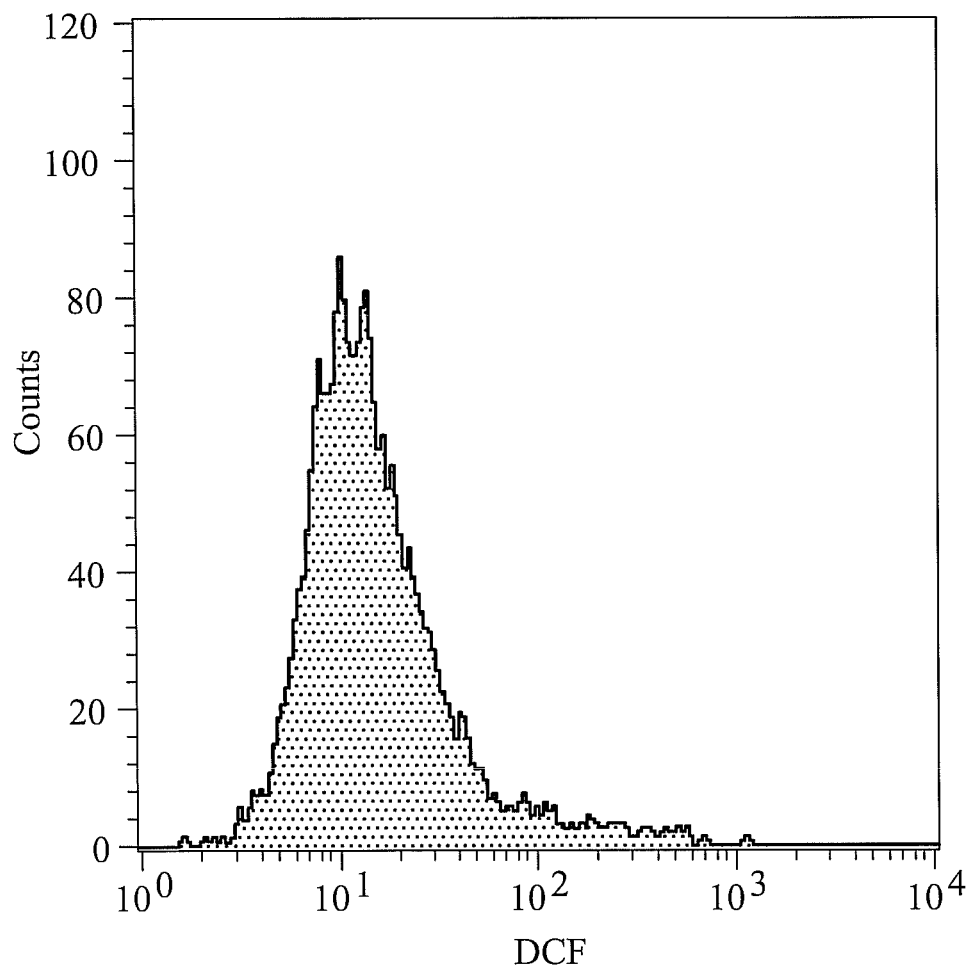

In blood, macrophage may be activated and produce reactive oxygen species upon recognizing a foreign substance. Thus, the invisibility of micelles to macrophage can be determined by measuring the reactive oxygen species contents. 2',7'-dichlorodihydrofluorescein diacetate (DCFDA) was added into a microphage culture (RAW 264.7). A micelle solution having concentration above CMC was then added and cultivated for 24 hours. If micelles activate macrophage, DCFDA may be converted into fluorescent DCF (2',7'-Dichlorofluorescin) by reactive oxygen species and its fluorescent intensity is directly proportional to reactive oxygen species contents. Finally, the invisibility of micelles was obtained by measurement with a flow cytometer. The fluorescent intensity of DCF in various conditions is shown in FIGS. 4-6.

Figure 4:
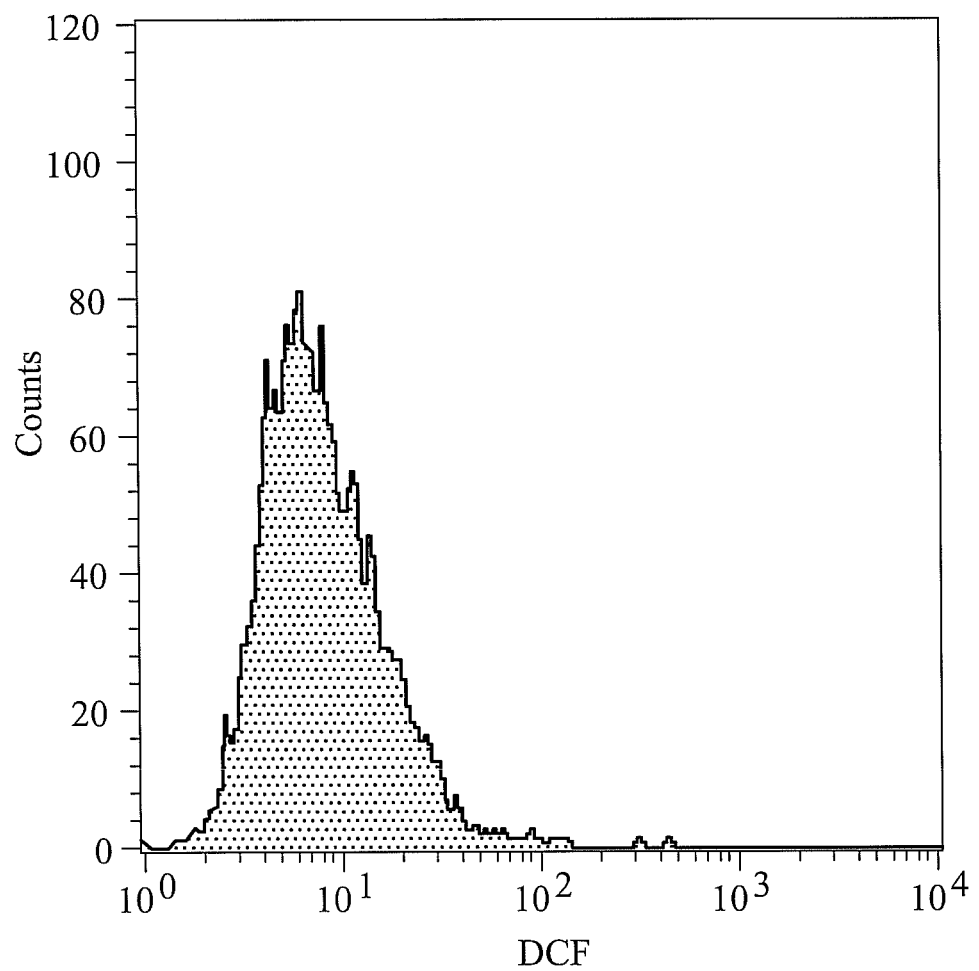
FIGS. 4-6 shows mean fluorescent intensity of DCF under various conditions.

FIG. 4 shows a mean fluorescent intensity of 9.39 without addition of micelles. FIG. 5 shows a mean fluorescent intensity of 10.8 with addition of micelles (PEG-PCL-PC2). FIG. 6 shows a mean fluorescent intensity of 20.13 with addition of 1 μm PMA for 24-hour activation. Due to the mean fluorescent intensity between (a) and (b) are similar, we can assert that the micelles are invisible.

Example 8

Preparation of Polymeric Nanoparticle 10 mg E50C19-PC was added into 1 mL dimethyl sulfoxide (DMSO) and stirred. After freeze-drying, 1 ml and 10% sucrose removed DMSO was added to hydrate. The freeze-dried solids were then dissolved to form a suspension. After ultra-sonicating for 10 min, polymer nanoparticles were formed. The particle size distribution of 120-200 nm was obtained by a laser particle size analyzer (Coulter N4 plus).

Example 9

Preparation of Nanocarrier Containing Drugs

Camptothecin is a water insoluble drug and has solubility of only 3 μg/ml. 1 mg camptothecin and 10 mg E50C19-PC were added into 1 ml dimethyl sulfoxide (DMSO) and stirred. After DMSO was removed by freeze-drying, 1 ml and 10% sucrose was added to hydrate. The freeze-dried solids were then dissolved to form a suspension. After ultra-sonicating for 10 min, polymer nanoparticles containing camptothecin were formed. The suspension was then filtered with a 0.45 μm filter to remove un-encapsulated camptothecin crystals. The particle size distribution of 130-190 nm was obtained by a laser particle size analyzer (Coulter N4 plus). The camptothecin concentration of 0.9 mg/ml in a micelle solution was measured by a HPLC. The solubility of camptothecin was increased to 300 times.

Example 10

Hemolysis Test of Nanocarrier Containing Drugs

The toxicity of polymer micelles with and without camptothecin to erythrocyte was quantitatively analyzed by the ASTM F756 standard operation. The results shown in Table 3 shows that the nanocarriers are non-hymolytic.

TABLE 3

| Carrier types | Hemolytic index (%) | Hemolytic grade |
|---|---|---|
| PEG-PCL-PC1 (placebo) | −0.07 | Non-hemolytic |
| PEG-PCL-NS1 (placebo) | 0.85 | Non-hemolytic |
| PEG-PCL-NS2 (placebo) | 0.85 | Non-hemolytic |
| PEG-PCL-NS3 (placebo) | 0.00 | Non-hemolytic |
| PEG-PCL-NS4 (placebo) | 0.00 | Non-hemolytic |
| PEG-PCL-PC1 nanocarrier containing camptothecin | 0.44 | Non-hemolytic |
| Camptothecin | 5.84 | slight hemolysis |

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A nanocarrier, comprising:
   a nanoparticle comprising one or more block copolymers, wherein the block copolymer comprises a hydrophobic block, a hydrophilic block bonded to the hydrophobic block, and one zwitterion, wherein the zwitterion is only bonded to the hydrophobic block, and the zwitterion has one positive charge and one negative charge, wherein the nanoparticle has a hydrophobic interior and hydrophilic surface, wherein the hydrophobic block comprises polycaprolactone (PCL), polyvalerolactone (PVL), poly(lactide-co-glycolide) (PLGA), polylactic acid (PLA), polybutyrolactone (PBL), polyglycolide, or polypropiolactone (PPL), and the hydrophilic block comprises polyethylene glycol (PEG), hyaluronic acid (HA), or poly-γ-glutamic acid (PGA); and
   an active substance encapsulated in the particle, wherein the nanoparticle has a diameter of about 20-1,000 nm.

2. The nanocarrier as claimed in claim 1, wherein the active substance comprises water insoluble drugs, growth factors, genes, or water insoluble cosmetic substances.

3. The nanocarrier as claimed in claim 1, wherein the active substance comprises camptothecin or derivatives thereof.

4. The nanocarrier as claimed in claim 1, wherein the active substance comprises water insoluble ingredients for skin care.

5. The nanocarrier as claimed in claim 1, wherein the nanocarrier is delivered by oral, transdermal administration, injection, or inhalation.

* * * * *

UNITED STATES PATENT AND TRADEMARK OFFICE
CERTIFICATE OF CORRECTION

PATENT NO. : 8,940,333 B2  
APPLICATION NO. : 12/053327  
DATED : January 27, 2015  
INVENTOR(S) : Ming-Fa Hsieh et al.

Page 1 of 1

It is certified that error appears in the above-identified patent and that said Letters Patent is hereby corrected as shown below:

On the title page item 75 the name of the second inventor should be corrected from "Hsuen-Tseng Cha'ng" to --Hsuen-Tseng Chang--.

Signed and Sealed this
Fourth Day of August, 2015

Michelle K. Lee
*Director of the United States Patent and Trademark Office*